United States Patent [19]

Rasberger

[11] 4,383,950
[45] May 17, 1983

[54] PHOSPHITE STABILIZERS

[75] Inventor: Michael Rasberger, Riehen, Switzerland

[73] Assignee: Ciba-Geigy Corporation, Ardsley, N.Y.

[21] Appl. No.: 311,138

[22] Filed: Oct. 14, 1981

Related U.S. Application Data

[63] Continuation of Ser. No. 137,146, Apr. 4, 1980, abandoned, which is a continuation of Ser. No. 58,048, Jul. 16, 1979, abandoned.

[30] Foreign Application Priority Data

Jul. 27, 1978 [CH] Switzerland ..................... 8085/78

[51] Int. Cl.³ ............................................. C07F 9/145
[52] U.S. Cl. .................................... 260/967; 524/151
[58] Field of Search ........................................ 260/967

[56] References Cited

U.S. PATENT DOCUMENTS

| | | | |
|---|---|---|---|
| 2,493,597 | 1/1950 | Rothrock et al. | 260/45.7 |
| 2,733,226 | 1/1956 | Hunter | 260/29.7 |
| 2,951,052 | 8/1960 | Darby | 260/23 |
| 2,997,454 | 8/1961 | Leistner et al. | 524/151 |
| 3,039,993 | 6/1962 | Friedman | 260/45.8 |
| 3,189,570 | 6/1965 | Paulin | 524/151 |
| 3,290,392 | 12/1966 | Ecke et al. | 260/45.95 H |
| 3,305,520 | 2/1967 | Fritz et al. | 260/45.7 PH |
| 3,498,946 | 3/1970 | Calkins | 260/45.7 PH |
| 3,960,758 | 6/1976 | Witte et al. | 252/404 |

FOREIGN PATENT DOCUMENTS

| | | |
|---|---|---|
| 2702661 | 2/1976 | Fed. Rep. of Germany . |
| 2606358 | 9/1976 | Fed. Rep. of Germany . |
| 1388246 | 6/1965 | France . |
| 1295746 | 11/1972 | United Kingdom . |
| 1298248 | 11/1972 | United Kingdom . |
| 366215 | 4/1973 | U.S.S.R. . |

Primary Examiner—V. P. Hoke
Attorney, Agent, or Firm—Luther A. R. Hall

[57] ABSTRACT

Compounds of the general formula (I)

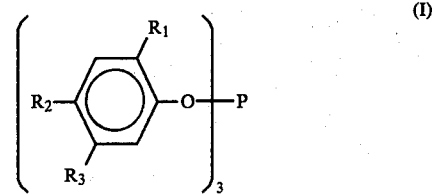

in which $R_1$ is an α-branched alkyl group having 3 to 12 carbon atoms, cyclohexyl, phenyl or α,α-dimethylbenzyl and $R_2$ is methyl, isopropyl, tert.-butyl, tert.-pentyl, 1,1,3,3-tetramethylbutyl, nonyl, 1,1,3,3,5,5-hexamethylhexyl or α,α-dimethylbenzyl, only one of $R_1$ and $R_2$ being 1,1,3,3-tetramethylbutyl and at least one of $R_1$ and $R_2$ possessing at least 8 carbon atoms, and $R_3$ is hydrogen or methyl, or $R_3$ together with $R_2$ is 1,1,3,3-tetramethyl-1,3-propylene, are suitable as stabilizers for organic material to protect it against thermo-oxidative and light-induced degradation.

3 Claims, No Drawings

PHOSPHITE STABILIZERS

This is a continuation of application Ser. No. 137,146, filed on Apr. 4, 1980, now abandoned, which in turn is a continuation of application Ser. No. 58,048, filed on July 16, 1979, now abandoned.

The present invention relates to novel substituted triaryl phosphites, their use as stabilisers and costabilisers to counter thermo-oxidative and light-induced degradation of organic material and to the organic material stabilised with these phosphites.

The esters of phosphorous acid are important for the stabilisation of organic material and have been widely described in the literature. Thus, for example, it is known from German Offenlegungsschrift No. 2,606,358 to use symmetrical alkylated triaryl phosphites in polyolefins.

Novel triaryl phosphites have now been found which better satisfy the high demands which have to be met by a stabiliser than do known compounds. The novel substances are distinguished, in particular, by the fact that they possess a combination of very diverse valuable properties, such as high storage stability, stability to hydrolysis, stability to extraction and a stabilising action coupled with excellent coloristic properties, low volatility and good compatibility and emulsifiability. The compounds according to the invention have the general formula I

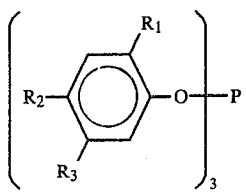
(I)

in which $R_1$ is an α-branched alkyl group having 3–12 C atoms, cyclohexyl, phenyl or α,α-dimethylbenzyl and $R_2$ is methyl, isopropyl, tert.-butyl, tert.-pentyl, 1,1,3,3-tetramethylbutyl, nonyl, 1,1,3,3,5,5-hexamethylhexyl or α,α-dimethylbenzyl, only one of $R_1$ and $R_2$ being 1,1,3,3-tetramethylbutyl and at least one of $R_1$ and $R_2$ possessing at least 8 C atoms, and $R_3$ is hydrogen or methyl, or $R_3$ together with $R_2$ is 1,1,3,3-tetramethyl-1,3-propylene.

As an α-branched alkyl group having 3–12 C atoms, $R_1$ is, for example, isopropyl, sec.-butyl, tert.-butyl, 1-methylbutyl, tert.-pentyl, 1,1-dimethylbutyl, 1,1,3,3-tetramethylbutyl, 1-ethylheptyl, 1-methyloctyl, 1,1-dimethylheptyl, 1-methylnonyl or 1,1,3,3,5,5-hexamethylhexyl. Tert.-alkyl groups, such as tert.-butyl, tert.-pentyl, 1,1,3,3-tetramethylbutyl or 1,1,3,3,5,5-hexamethylhexyl, are preferred as $R_1$.

Preferred compounds of the formula I are those in which $R_1$ is an α-branched alkyl group having 3–12 C atoms or α,α-dimethylbenzyl and $R_2$ is methyl, isopropyl, tert.-butyl, tert.-pentyl, 1,1,3,3-tetramethylbutyl, nonyl, 1,1,3,3,5,5-hexamethylhexyl or α,α-dimethylbenzyl, only one of $R_1$ and $R_2$ being 1,1,3,3-tetramethylbutyl and at least one of $R_1$ and $R_2$ possessing at least 8 C atoms, and $R_3$ is hydrogen.

Particularly preferred compounds of the formula I are those in which $R_1$ is tert.-butyl, tert.-pentyl, 1,1,3,3-tetramethylbutyl, 1,1,3,3,5,5-hexamethylhexyl or α,α-dimethylbenzyl and $R_2$ is tert.-butyl, tert.-pentyl, 1,1,3,3-tetramethylbutyl, 1,1,3,3,5,5-hexamethylhexyl or α,α-dimethylbenzyl, only one of $R_1$ and $R_2$ being 1,1,3,3-tetramethylbutyl and at least one of $R_1$ and $R_2$ possessing at least 8 C atoms, and $R_3$ is hydrogen.

Further preferred compounds of the formula I are those in which $R_1$ is 1,1,3,3-tetramethylbutyl, 1,1,3,3,5,5-hexamethylhexyl or α,α-dimethylbenzyl, and also those in which $R_2$ is 1,1,3,3-tetramethylbutyl, 1,1,3,3,5,5-hexamethylhexyl or α,α-dimethylbenzyl.

Examples of compounds of the formula I are:
(1) Tris-(2-tert.-butyl-4-tert.-octylphenyl)phosphite
(2) Tris-(2-tert.-butyl-4-[α,α-dimethylbenzyl]-phenyl)phosphite
(3) Tris-(2-tert.-butyl-4-tert.-dodecylphenyl)phosphite
(4) Tris-(2-tert.-pentyl-4-tert.-octylphenyl)phosphite
(5) Tris-(2-tert.-pentyl-4-[α,α-dimethylbenzyl]-phenyl)phosphite
(6) Tris-(2-isopropyl-4-tert.-octylphenyl)phosphite
(7) Tris-(2-cyclohexyl-4-tert.-octylphenyl)phosphite
(8) Tris-(2-phenyl-4-tert.-octylphenyl)phosphite
(9) Tris-(2-isopropyl-4-[α,α-dimethylbenzyl]-phenyl)phosphite
(10) Tris-(2-tert.-dodecyl-4-tert.-butylphenyl)phosphite
(11) Tris-(2-tert.-octyl-4-methylphenyl)phosphite
(12) Tris-(2-tert.-octyl-4-nonylphenyl)phosphite
(13) Tris-(2-tert.-dodecyl-4-tert.-octylphenyl)phosphite
(14) Tris-(2-tert.-dodecyl-4-[α,α-dimethylbenzyl]-phenyl)phosphite
(15) Tris-(2-isopropyl-4-tert.-dodecylphenyl)phosphite
(16) Tris-(2-tert.-octyl-4-tert.-butyl-5-methylphenyl)-phosphite
(17) Tris-(2-tert.-butyl-4-tert.-octyl-5-methylphenyl)-phosphite
(18) Tris-(1,1,3,3-tetramethyl-5-tert.-octyl-indan-6-yl)phosphite
(19) Tris-(2-tert.-butyl-4-[α,α-dimethylbenzyl]-5-methylphenyl)phosphite
(20) Tris-(2,4-di-tert.-dodecylphenyl)phosphite
(21) Tris-(2-tert.-octyl-4-tert.-butylphenyl)phosphite
(22) Tris-(2,4-di-[α,α-dimethylbenzyl]-phenyl)-phosphite In compounds (1)–(22) tert.-octyl is 1,1,3,3-tetramethylbutyl and tert.-dodecyl is 1,1,3,3,5,5-hexamethylhexyl.

The phosphites of the formula I are prepared by methods known per se, especially by esterification or trans-esterification methods, for example by reacting approximately three mols of a phenol of the formula II

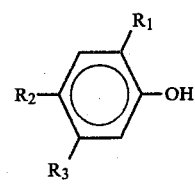
(II)

in which $R_1$, $R_2$ and $R_3$ are as defined above, with approximately one mol of a compound of the formula III $PX_3$ (III), in which X is a reactive group.

A reactive group X is, for example, halogen, especially chlorine; however, it can also be alkoxy or phenoxy.

The reaction can be carried out in a manner known per se, for example at −5° C. to 80° C., or by heating, preferably to above about 80° C., for example 80°–170° C. The reaction can be carried out without a solvent or in the presence of an inert solvent, such as aprotic solvents, for example ligroin, toluene, xylene, hexane, cyclohexane, dimethylformamide, dimethylacetamide, sulfolane, acetonitrile, dioxan, di-n-butyl ether, 1,2-dichloroethane, dimethylsulfoxide, ethyl acetate, methyl ethyl ketone, nitrobenzene, nitromethane, tetrahydrofuran, chloroform or trichloroethylene. If X is halogen, the reaction is advantageously carried out in the presence of a base, such as sodium carbonate or an amine, for example triethylamine, pyridine or N,N-dimethylaniline. Amine bases employed in excess can at the same time serve as solvents.

The starting materials of the formulae II and III are known or, if they are novel, can be prepared analogously to known starting materials.

According to the present invention, the compounds of the formula I can be used as stabilisers for plastics and elastomers to protect them against damage due to the action of oxygen, light and heat, especially during processing. Examples of such plastics are the polymers listed on pages 12–14 of German Offenlegungsschrift 2,456,864.

Suitable substrates are, for example:

1. Polymers which are derived from mono-unsaturated or di-unsaturated hydrocarbons, such as polyolefins, for example polyethylene, which can be crosslinked, polypropylene, polyisobutylene, polymethylbut-1-ene, polymethylpent-1-ene, polyisoprene, polybutadiene or polyisobutylene.

2. Mixtures of the homopolymers listed under 1, for example mixtures of polypropylene and polyethylene, of polypropylene and polybut-1-ene or of polypropylene and polyisobutylene.

3. Copolymers of the monomers on which the homopolymers listed under 1 are based, such as ethylene/propylene copolymers, propylene/butene copolymers, propylene/isobutylene copolymers or ethylene/but-1-ene copolymers and also terpolymers of ethylene and propylene with a diene, for example hexadiene, dicyclopentadiene or ethylidenenorbornene.

4. Polystyrene.

5. Copolymers of styrene and of α-methylstyrene, such as styrene/butadiene copolymers, styrene/acrylonitrile copolymers, styrene/acrylonitrile/methyl methacrylate copolymers, styrene/acrylonitrile/acrylate copolymers, styrene/acrylonitrile copolymers modified with acrylate polymers to give increased impact strength and styrene polymers modified with EPDM to give increased impact strength.

6. Graft copolymers of styrene, for example the graft polymer of styrene on polybutadiene, the graft polymer of styrene and acrylonitrile on polybutadiene and mixtures thereof with the copolymers listed under 5, which in general are termed acrylonitrile/butadiene/styrene or ABS plastics.

7. Halogen-containing vinyl polymers, such as polyvinyl chloride, polyvinylidene chloride, polyvinyl fluoride, polychloroprene, chlorinated rubbers, vinyl chloride/vinylidene chloride copolymers, vinyl chloride/vinyl acetate copolymers and vinylidene chloride/vinyl acetate copolymers.

8. Polymers which are derived from α,β-unsaturated acids and their derivatives, such as polyacrylates and polymethacrylates, polyacrylamides and polyacrylonitrile.

9. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyrate, polyallyl phthalate, polyallylmelamine and their copolymers with other vinyl compounds, such as ethylene/vinyl acetate copolymers.

10. Homo- and co-polymers which are derived from epoxides, such as polyethylene oxide or the polymers which are derived from bis-glycidyl ethers.

11. Polyacetals, such as polyoxymethylene, and also those polyoxymethylenes which contain ethylene oxide as the comonomer.

12. Polyalkylene oxides, such as polyoxyethylene, polypropylene oxide or polyisobutylene oxide.

13. Polyphenylene oxides.

14. Polyurethanes and polyureas.

15. Polycarbonates.

16. Polysulfones.

17. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

18. Polyesters which are derived from dicarboxylic acids and dialcohols and/or from hydroxycarboxylic acids or the corresponding lactones, such as polyethylene glycol terephthalate and poly-1,4-dimethylolcyclohexane terephthalate.

19. Crosslinked polymers which are derived from aldehydes on the one hand and from phenols, ureas and melamines on the other hand, such as phenol/formaldehyde resins, urea/formaldehyde resins and melamine/formaldehyde resins.

20. Alkyd resins, such as glycerol/phthalic acid resins and their mixtures with melamine/formaldehyde resins.

21. Unsaturated polyester resins which are derived from copolyesters of saturated and unsaturated dicarboxylic acids with polyhydric alcohols and vinyl compounds as crosslinking agents, and also their halogen-containing modifications of low combustibility.

22. Naturally occurring polymers, such as cellulose, rubber and proteins, and also their polymer-homologously chemically modified derivatives, such as cellulose acetates, cellulose propionates and cellulose butyrates and the cellulose ethers, such as methylcellulose.

23. Naturally occurring and synthetic organic materials which are pure monomeric compounds or mixtures of such compounds, for example mineral oils, animal and vegetable fats, oils and waxes, or oils, fats and waxes based on synthetic esters, and also mixtures of synthetic esters with mineral oils in any weight ratios.

The phosphites of the formula I are incorporated into the substrates in a concentration of 0.005 to 5% by weight, based on the material to be stabilised.

Preferably, 0.01 to 1.0, and particularly preferentially 0.02 to 0.5,% by weight of the compounds, based on the material to be stabilised, is incorporated into the latter. Incorporation can be effected, for example, by mixing in the phosphites of the formula I, and, if desired, further additives, by the methods customary in the art, before or during shaping, or by applying the dissolved or dispersed compounds to the polymer, with subsequent evaporation of the solvent if necessary.

The novel compounds can also be added to the plastics to be stabilised in the form of a masterbatch which contains these compounds, for example in a concentration of 2.5 to 25% by weight.

In the case of crosslinked polyethylene, the compounds are added prior to crosslinking.

The materials stabilised in this way can be used in very diverse forms, for example as films, fibres, tapes, moulding compositions or profiles or as binders for lacquers, adhesives or putties.

In practice, the phosphites of the formula I can be employed together with other stabilisers. Synergistic mixtures can arise. The present invention therefore also relates to the organic materials which are stabilised by the addition of 0.005 to 0.5% by weight of a phosphite of the formula I and which, if desired, can also contain further additives.

The combination of the phosphite according to the invention with a phenolic antioxidant is particularly preferred.

Examples of phenolic compounds are:

1. Simple 2,6-dialkylphenols, for example 2,6-di-tert.-butyl-4-methylphenol, 2,6-di-tert.-butyl-4-methoxymethylphenol or 2,6-di-tert.-butyl-4-methoxyphenol.

2. Bisphenols, for example 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-4-n-dodecyl-mercaptobutane, 1,1,5,5-tetra-(5-tert.-butyl-4-hydroxy-2-methylphenyl)-pentane, ethylene glycol bis-[3,3-bis-(3'-tert.-butyl-4'-hydroxyphenyl)butyrate], 1,1-bis-(3,5-dimethyl-2-hydroxyphenyl)-3-(n-dodecylthio)-butane or 4,4'-thio-bis-(6-tert.-butyl-3-methylphenol).

3. Hydroxybenzyl aromatic compounds, for example 1,3,5-tris-(3,5-di-tert.-butyl-4-hydroxybenzyl)-2,4,6-trimethylbenzene, dioctadecyl 2,2-bis-(3,5-di-tert.-butyl-4-hydroxybenzyl)-malonate, 1,3,5-tris-(3,5-di-tert.-butyl-4-hydroxybenzyl)isocyanurate or diethyl 3,5-di-tert.-butyl-4-hydroxybenzyl-phosphonate.

4. Amides of β-(3,5-di-tert.-butyl-4-hydroxyphenyl)-propionic acid, for example 1,3,5-tris-(3,5-di-tert.-butyl-4-hydroxyphenyl-propionyl)-hexahydro-s-triazine or N,N'-di-(3,5-di-tert.-butyl-4-hydroxyphenyl-propionyl)-hexamethylenediamine.

5. Esters of β-(3,5-di-tert.-butyl-4-hydroxyphenyl)-propionic acid with monohydric or polyhydric alcohols, for example with methanol, octadecanol, 1,6-hexanediol, ethylene glycol, thiodiethylene glycol, neopentylglycol, pentaerythritol or tris-hydroxyethyl isocyanurate.

6. Spiro compounds, for example diphenolic spirodiacetals or -diketals, for example 2,4,8,10-tetraoxaspiro[5.5]undecane substituted in the 3,9-position by phenolic radicals, for example 3,9-bis-(3,5-di-tert.-butyl-4-hydroxyphenyl)-2,4,8,10-tetraoxaspiro[5.5]undecane or 3,9-bis-[1,1-dimethyl-2-(3,5-di-tert.-butyl-4-hydroxyphenyl)-ethyl]-2,4,8,10-tetraoxaspiro[5.5]undecane.

Particularly preferred phenolic compounds are: 1,3,5-tri-(3,5-di-tert.-butyl-4-hydroxybenzyl)-2,4,6-trimethylbenzene, pentaerythritol tetra-[3-(3,5-di-tert.-butyl-4-hydroxyphenyl)-propionate], n-octadecyl β-(3,5-di-tert.-butyl-4-hydroxyphenyl)-propionate, thiodiethylene glycol β-[4-hydroxy-3,5-di-tert.-butyl-phenyl]-propionate, 2,6-di-tert.-butyl-4-methyl-phenol, 1,1,3-tris-(5-tert.-butyl-4-hydroxy-2-methylphenyl)-butane, 2,2'-methylene-bis-(6-tert.-butyl-4-methylphenol), 4,4'-thio-bis-(6-tert.-butyl-3-methylphenol), ethylene glycol bis-[(3,3-bis-3'-tert.-butyl-4'-hydroxy-phenyl)-butyrate], 1,3,5-tris-(3',5'-di-tert.-butyl-4-hydroxybenzyl)isocyanurate and 1,1-bis-(2'-methyl-4'-hydroxy-5'-tert.-butylphenyl)-butane.

The triaryl phosphite and the phenolic antioxidant are incorporated in a ratio of 10:1 to 1:5, preferably 5:1 to 1:2 and in particular 3:1 to 1:1.

Examples of further additives which can be employed together with the phosphite according to the invention are: UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acid and acrylates, and also nickel compounds, sterically hindered amines, oxalic acid diamides, metal deactivators, compounds which destroy peroxide, polyamide stabilisers, thioethers, basic co-stabilisers, nucleating agents or other additives, for example plasticisers, lubricants, emulsifiers, fillers, carbon black, asbestos, kaolin, talc, glass fibres, pigments, fluorescent brighteners, flameproofing agents or antistatic agents.

The following examples illustrate the invention in more detail.

EXAMPLE 1

6.85 g of phosphorus trichloride are added dropwise at 100° C. to 33.33 g (0.15 mol) of 2-tert.-octyl-4-tert.-butylphenol and 0.17 ml of dimethylformamide and the mixture is then warmed to 140° C.; the reaction mixture is kept at this temperature for 4 hours and the reaction is then brought to completion in the course of two hours at 180° C. under a waterpump vacuum. The reaction mixture is cooled and the product is crystallised out by adding acetone. The tris-(2-tert.-cetyl-4-tert.-butylphenyl)phosphite [tert.-octyl=1,1,3,3-tetramethylbutyl] thus obtained melts at 118° C. (Stabiliser 1).

EXAMPLE 2

Example 1 is repeated using an equimolar amount of 2,4-di-(α,α-dimethylbenzyl)-phenol, yielding tris-[2,4-di-(α,α-dimethylbenzyl)-phenyl]phosphite in the form of an oily residue (Stabiliser 2) which has the following elementary analysis: calculated: C 84.8, H 7.42, P 3.04; found: C 85.0, H 7.8, P 2.8.

The compounds of the following examples were prepared by a procedure analogous to that described under Example 1.

EXAMPLE 3

Tris-(2-tert.-octyl-4-methylphenyl)phosphite. Melting point: 125° C. (Stabiliser 3).

EXAMPLE 4

Tris-(2-tert.-octyl-4-nonylphenyl)phosphite (oil) (Stabiliser 4)

Analysis: calculated: C 80.8, H 11.5, P 3.02; found: C 81.0, H 11.4, P 2.9.

EXAMPLE 5

100 parts of high molecular weight polyethylene powder (Lupolen 5260 from BASF) were mixed with 0.05 part of pentaerythritol tetrakis-[3-(3,5-di-tertiary butyl-4-hydroxyphenyl)-propionate] and 0.1 part of the compounds according to the invention listed in the table given below, and the mixtures were kneaded in a Brabender plastograph at 220° C. and 50 revolutions per minute. During this time, the resistance to kneading is recorded continuously as torque. During the kneading period, the polymer starts to crosslink after remaining constant for a relatively long time and this crosslinking can be determined with the aid of the rapid increase in the torque. The effectiveness of the stabilisers manifests itself in a prolongation of the period of constancy.

In addition, after kneading in the Brabender plastograph the Yellowness Index (Y.I.) according to ASTM D-1925/6-3T was measured. Higher Y.I. figures indicate greater discoloration.

| Stabiliser | Time in minutes before there is a change in the torque | Y.I. |
|---|---|---|
| none | 3 | 8.2 |
| No. 1 | 8 | 0.69 |
| No. 2 | 8 | −1.5 |
| No. 3 | 12 | 3.5 |
| No. 4 | 7½ | 3.6 |

What is claimed is:

1. A compound of formula I

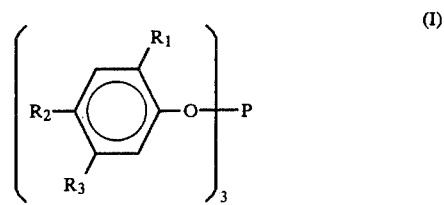

wherein
R$_1$ is 1,1,3,3-tetramethylbutyl,
R$_2$ is methyl, isopropyl, tert-butyl, tert-amyl, nonyl or 1,1,3,3,5,5-hexamethylhexyl, and R$_3$ is hydrogen or methyl, or R$_3$ together with R$_2$ is 1,1,3,3-tetramethyl-1,3-propylene.

2. A compound according to claim 1, of formula I, wherein R$_2$ is tert-butyl, tert-amyl or 1,1,3,3,5,5-hexamethylhexyl, and R$_3$ is hydrogen.

3. A compound according to claim 1 which is tris-[2-(1,1,3,3-tetramethylbutyl)-4-tert-butylphenyl]phosphite, tris-[2-(1,1,3,3-tetramethylbutyl)-4-methylphenyl]phosphite, tris-[2-(1,1,3,3-tetramethylbutyl)-4-nonylphenyl]phosphite or tris-[1,1,3,3-tetramethyl-5-(1,1,3,3-tetramethylbutyl)-indan-6-yl]phosphite.

* * * * *